United States Patent
Bos et al.

(10) Patent No.: US 11,666,209 B2
(45) Date of Patent: *Jun. 6, 2023

(54) VIDEO ENDOSCOPY (71) Applicant: KARL STORZ Imaging, Inc., Goleta, CA (US)

(72) Inventors: Pieter Henderikus Andries Bos, Tuttlingen (DE); Timothy King, Goleta, CA (US)

(73) Assignee: KARL STORZ Imaging, Inc., Goleta, CA (US)

( * ) Notice: Subject to any disclaimer, the term of this patent is extended or adjusted under 35 U.S.C. 154(b) by 199 days.

This patent is subject to a terminal disclaimer.

(21) Appl. No.: 17/078,887

(22) Filed: Oct. 23, 2020

(65) Prior Publication Data
US 2021/0038066 A1 Feb. 11, 2021

Related U.S. Application Data (63) Continuation of application No. 16/019,020, filed on Jun. 26, 2018, now Pat. No. 10,835,116, which is a
(Continued)

(51) Int. Cl.
*A61B 1/00* (2006.01)
*A61B 1/267* (2006.01)
(Continued)

(52) U.S. Cl.
CPC ........ *A61B 1/2673* (2013.01); *A61B 1/00006* (2013.01); *A61B 1/00009* (2013.01); *A61B 1/00045* (2013.01); *A61B 1/045* (2013.01); *A61B 1/0655* (2022.02); *A61B 7/023* (2013.01); *G10L 25/48* (2013.01); *H04N 5/2621* (2013.01); *H04N 23/56* (2023.01); *H04N 23/60* (2023.01); *H04N 23/72* (2023.01); *H04N 23/73* (2023.01); *H04N 23/74* (2023.01); *H04N 23/76* (2023.01); *H04N 23/951* (2023.01); *A61B 7/008* (2013.01);
(Continued)

(58) Field of Classification Search
CPC ..... A61B 1/267; A61B 1/2673; A61B 1/2676; A61B 1/04
See application file for complete search history.

(56) References Cited

U.S. PATENT DOCUMENTS 10,835,116 B2 * 11/2020 Bos ................ A61B 1/0655
2017/0064178 A1 3/2017 Kagawa et al.

FOREIGN PATENT DOCUMENTS

CN 106256123 A 12/2016

OTHER PUBLICATIONS

China National Intellectual Property Administration, First Office Action (Chinese Language), dated Jan. 19, 2023, pp. 1-12, China.
(Continued)

*Primary Examiner* — Eduardo C Robert
*Assistant Examiner* — Christina Negrellirodriguez
(74) *Attorney, Agent, or Firm* — David Villalpando (57) ABSTRACT

A system, method, scope device, and camera control module device for a video endoscopy system, to enable scopes to operate with a rolling shutter-type image sensor. With selected pulsing of a strobe light, subset image data from adjacent rolling-shutter frames is selected, gain compensated for missing light and combined into a new single video frame.

14 Claims, 7 Drawing Sheets

Related U.S. Application Data continuation-in-part of application No. 15/814,779, filed on Nov. 16, 2017, now Pat. No. 10,499,803.

(51) Int. Cl.

| | | |
|---|---|---|
| *A61B 7/02* | (2006.01) | |
| *G10L 25/48* | (2013.01) | |
| *A61B 1/045* | (2006.01) | |
| *H04N 5/262* | (2006.01) | |
| *A61B 1/06* | (2006.01) | |
| *H04N 23/56* | (2023.01) | |
| *H04N 23/60* | (2023.01) | |
| *H04N 23/72* | (2023.01) | |
| *H04N 23/73* | (2023.01) | |
| *H04N 23/74* | (2023.01) | |
| *H04N 23/76* | (2023.01) | |
| *H04N 23/951* | (2023.01) | |
| *G10L 25/66* | (2013.01) | |
| *G10L 25/90* | (2013.01) | |
| *A61B 7/00* | (2006.01) | |
| *H04N 23/50* | (2023.01) | |

(52) U.S. Cl.
CPC ........ *G10L 25/66* (2013.01); *G10L 2025/903* (2013.01); *H04N 23/555* (2023.01)

(56) References Cited

OTHER PUBLICATIONS

China National Intellectual Property Administration, First Office Action (Translation by Xinyu Liu), dated Jan. 19, 2023, pp. 1-20, China.

\* cited by examiner

VIDEO ENDOSCOPY

CROSS REFERENCE TO RELATED APPLICATION

This application is a continuation of U.S. application Ser. No. 16/019,020 filed on Jun. 26, 2018, and now issued as U.S. Pat. No. 10,835,116 B2 on Nov. 17, 2020, which is a continuation-in-part of U.S. application Ser. No. 15/814,779 filed on Nov. 16, 2017, and now issued as U.S. Pat. No. 10,499,803 B2 on Dec. 10, 2019, the entire contents of each of which are incorporated herein by reference.

TECHNICAL FIELD OF THE INVENTION

The invention relates generally to the field of medical imaging scopes and more specifically to video endoscopy cooperating selectively timed illumination.

BACKGROUND OF THE INVENTION

Video endoscopy is a medical examination procedure that combines video observation and display with a specially timed illumination. For example, video stroboscopy may be used to evaluate the function of the vocal cords, or larynx. During vocalization such as speech and singing, the vocal folds in the larynx vibrate too rapidly to discern the movement under constant lighting conditions. Stroboscopy solves this problem by using a strobe light to illuminate the larynx. The strobe light emits light flashes at a rate either matched with or very slightly different than the vibration base frequency of the vocal folds, causing the folds to appear to move in slow motion when viewed through the scope. An examiner may then observe the movement and function of the larynx as a patient makes sounds.

Such stroboscopic rhino laryngoscopy exams are typically performed with a flexible endoscope passed through the nose. The endoscope used may also be called a stroboscopic laryngoscope, with the procedure referred to as laryngeal stroboscopy. The scope contains an optical system and a small camera for observation and recording of the exam for later review.

In existing systems, the process of laryngeal stroboscopy typically requires a global exposure type shutter arrangement for the scope camera, with the strobe light exposing the entire image sensor array at the desired position of the vocal cords during vibration. However, rolling shutter type image sensors arrays, including many CMOS image sensors, may offer higher resolution capabilities at a comparably cheaper price point to global shutter type imaging arrays. Further, the use of rolling shutter type arrays in laryngeal stroboscopy would allow interoperability of designs across existing scope platforms, reduce costs, and enhance capabilities of scopes.

What is needed, therefore, are improved systems and techniques for video endoscopy and specially timed illumination that enable better use of rolling shutter type image sensors in scopes.

SUMMARY OF THE INVENTION

A video endoscopy system includes an imager, a light source, an exposure controller, and a digital line gain module. The imager generates a first frame and a second frame of a plurality of video frames using a rolling shutter. The light source generates pulses of light based on a desired frequency. The exposure controller adjusts a duration and position in time of the pulses based on the desired frequency during the first and second frames. The digital line gain module selectively applies a digital line gain to at least a portion of the first frame and a portion of the second frame, the digital line gain applied to pixels on one or more lines of the portions of the first and second frames, based on a gap time between the first frame and the second frame and the duration and position in time of the pulses.

In other features, the video endoscopy system includes a frame gain module that selectively applies a digital frame gain to a combined frame generated from the portions of the first and second frames, the digital frame gain applied to pixel values of the combined frames, based on the duration of the pulses and a desired duration of the pulses.

In still other features, the video endoscopy system light source generates two or more light pulses during the first and second frames. In yet other features, the first and second frames are adjacent frames.

In other features, the video endoscopy system includes a frame combination module that combines portions of the first and second frames to form the combined frame after application of the digital line gain. In yet other features, an output frame module generates an output frame based on the digital frame gain and the combined frame.

In still other features, the video endoscopy system includes audio processing circuitry that determines the desired frequency using a vocalization based on an audio signal.

A method of operating a video endoscopy system includes the steps of generating a first frame and a second frame of a plurality of video frames using a rolling shutter; generating pulses of light at a desired frequency; adjusting a duration and position in time of the pulses based on the desired frequency during the first and second frames; and selectively applying a digital line gain to at least a portion of the first frame and a portion of the second frame, the digital line gain applied to pixel values on one or more lines of the portions of the first and second frames, based on a gap time between the first frame and the second frame and the duration and position in time of the pulses.

In other features, the method includes selectively applying a digital frame gain to a combined frame generated from the portions of the first and second frames, the digital frame gain applied to pixel values of the combined frame, based on the duration of the pulses and a desired duration of the pulses.

In still other features, the method includes generating two or more light pulses during the first and second frames. In yet other features, the first and second frames are adjacent frames.

In other features the method includes combining portions of the first and second frames to form the combined frame after application of the digital line gain. In yet other features, the method includes generating an output frame based on the digital frame gain and the combined frame.

In still other features, the method includes determining the desired frequency using a vocalization based on an audio signal.

In some implementations of the various aspects, the functionality or process includes creating the two or more light emitter pulses in a sequence in which the pulses are spaced at a time period that is the inverse of the base frequency of the vocalization, and in which a gap occurs in the sequence such that at least one pulse is partly or completely missing in order to fully expose image sensor array lines for producing the two subsets. This leads to the fact that certain parts of the image sensor array are less exposed in comparison to other parts that are fully exposed.

These and other features of the invention will be apparent from the following description of the preferred embodiments, considered along with the accompanying drawings.

BRIEF DESCRIPTION OF THE DRAWINGS

The present invention will become more fully understood from the detailed description given herein and the accompanying drawings which are given by way of illustration only, and thus are not limitative of the present invention, and wherein.

DETAILED DESCRIPTION OF EXAMPLE EMBODIMENTS

The present invention provides a system, method, scope device, and camera control module device for a stroboscopic laryngoscope to enable scopes able to operate with a rolling shutter-type image sensor. With selected pulsing of a strobe light, subset image data from adjacent rolling-shutter frames is selected and combined into a new single video frame.

Figure 1:
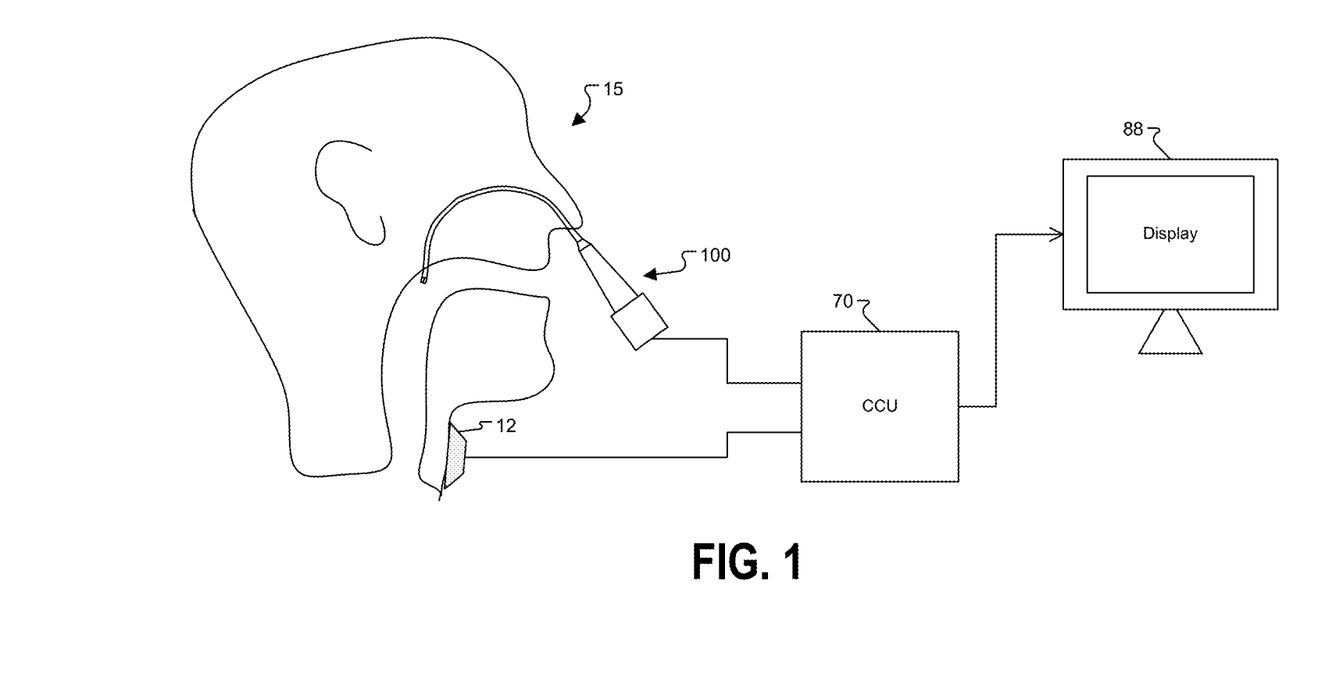
FIG. 1 is diagram showing set up of a medical stroboscopy system.

FIG. 1 is a diagram showing the set up of a medical stroboscopy system according to an example embodiment. To conduct an examination, the patient 15 preferably has a microphone 12 attached to their throat near the larynx or mounted at a suitable location for detecting the patient's vocalizations during the exam, such as speech and singing certain tones as requested by the examiner. The diagram shows a flexible stroboscopic laryngoscope 100 passed through the patient's nose to point down the throat toward the larynx and vocal cords. Rigid or flexible scopes may instead be passed through the mouth to achieve a similar viewing angle. The scope 100 and microphone 12 are both connected to a camera control unit (CCU) 70 by cables, typically digital data transmission cables, which may also provide power. CCU 70 sends control commands to the scope and receives image data from the scope and audio data or signaling from the microphone.

The CCU has the capability to detect the base frequency of the vocal cord in order to generate a frequency for the LED light source, which is in phase with the audio frequency of the vocal cord. The camera can be a proximal head, rigid endoscope or flexible videoendoscope with a rolling shutter sensor used for medical purposes in the endoscopy. The CCU can also be built of sub modules, where for example the display or light source are separated modules. The data communication link functionality of the CCU may be separated into a link module that communicates with the scope device, while the image processing functionality may be included in a camera control module of the CCU.

Figure 2:
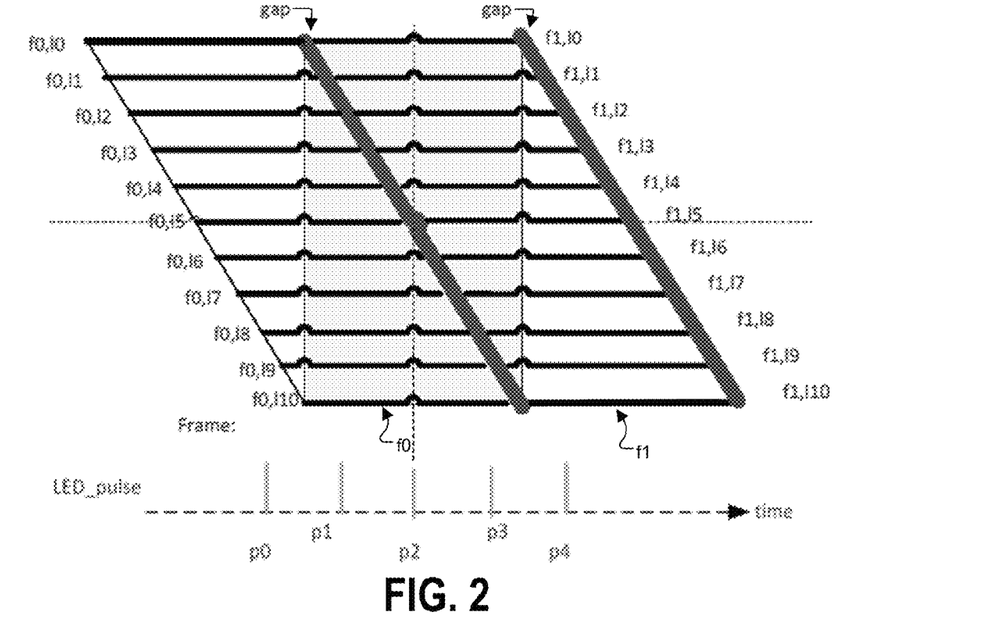
FIG. 2 and FIG. 3 show timing diagrams for a process of strobing the light source and reading the image sensor array with a rolling shutter.
Figure 3:
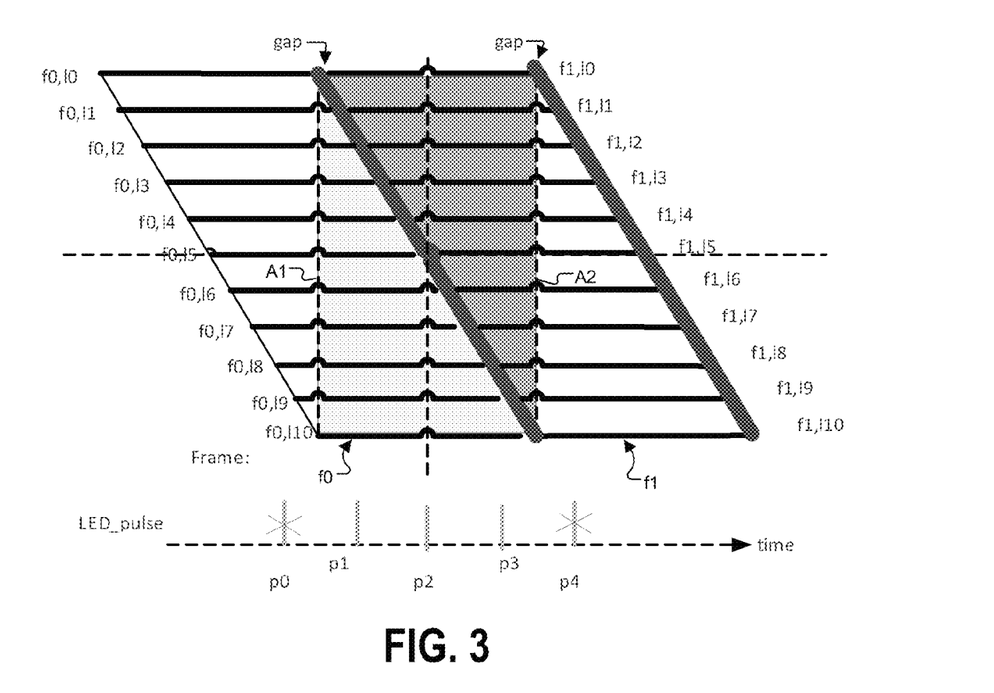

FIG. 2 and FIG. 3 show timing diagrams for a process of strobing the light source and reading the image sensor array with a rolling shutter. According to an example embodiment, the system generates video frames according to a rolling shutter concept as shown. The timing diagram of FIG. 2 shows the pulses p0-p4 of the scope light emitter LED (LED pulse time axis) as it relates to the reading of sensor array lines L0-L10 according to a rolling shutter scheme. The number of lines depends on the vertical resolution of the image sensor and is not limited to 10 lines. For example, a full HD sensor includes 1080 lines and a 4K sensor includes 2160 lines. The diagram shows two frames f0 and f1 which are exposed with the LED pulses p0-p4. The pulses expose lines being scanned in both depicted frames, f0 and f1, because the lines are scanned beginning at different times according to a rolling shutter scheme. The use of the scanned data is described further below.

As shown in FIG. 2 and FIG. 3, the diagrams include two frames f0 and f1, however in strobing mode the scheme is repeated for all frames. When these frames are exposed for the maximum of one frame there is a small gap as shown separating the two frames, where the frame is not exposed depending on the specific configuration of the sensor, which is different for each sensor. This non-exposed area takes place at the end of the exposure of a line, as shown twice in the diagrams. The shift from one line to the other is due to the architecture of the rolling shutter, where each frame line is exposed with a small shift after each other rolling through the entire frame. The LED pulses shown at the bottom are timed based on the audio frequency of the patient's vocal cord to expose the vocal cord. Typically, the pulses are strobed at a time interval inverse to the measured base frequency, as further discussed with regard to the process described below.

The diagram of FIG. 3 will be described further with reference to the process of FIG. 4, which shows a flowchart of a method for operating the stroboscopic scope system. At process block 402, the procedure is set up attaching the microphone to the patient's throat near the larynx or setting it in another suitable location to detect vocalization. The scope is inserted into the patient's throat or nose to view the larynx, and the procedure begins.

Next at block 404, the process measures a patient's vocalization, made under direction of the examining technician or doctor, with the microphone.

The exam typically includes the patient singing a variety of tones and making other vocalizations. At block 406, the CCU analyzes the audio data to determine the base frequency of the vocalization. This is typically done with a digital fast Fourier transforms (FFT) and frequency domain analysis of the result, for example to find the frequency with a maximum power level, or a local maximum, or other suitable frequency domain analysis. At block 408, the process selects a strobing frequency or time sequence for pulsing the strobe light of the scope based on the base frequency of the vocalization. Typically, the strobe timing is determined directly from the base frequency f, to perform strobing at 1/f, however this is not limiting, and different procedures may analyze other characteristics besides the base frequency and select appropriate strobing sequences accordingly.

At block 410, the process, on a continuous basis while observing the patient's vocal cords with the stroboscopic laryngoscope during the patient's vocalization, pulses the light emitter of the stroboscopic laryngoscope at time intervals selected based on the base frequency of the vocalization. Such pulses are seen in FIG. 2, where pulses p0-p4 are timed at the inverse of the base frequency (the separation time of the pulses is 1/f where f is the measure base frequency). As shown at block 410, the sequence of pulses is chosen such that two adjacent frames are exposed with at least two pulses. Often more pulses than the four depicted are used, for example at a frame rate of 30 fps, with a typical adult voice having a lowest base or fundamental frequency from 85 to 180 Hz for men and 165 to 255 Hz for women, and much higher base frequencies as the vocalization pitch increases, at higher base frequencies several pulses will occur in each frame. The duty cycle of the time period of such a strobe pulse may be less than 100%.

Next at block 412 the process includes reading image data from the image sensor array of the stroboscopic laryngoscope according to a rolling shutter process. In the depicted version of FIG. 2, the rolling shutter process reads the image data from lines of the image sensor array, each line of the frames f0 and f1 offset in time such that at least two of the two or more light emitter pulses each expose sensor pixels in both first and second adjacent frames simultaneously.

FIG. 3 shows the use of the data in constructing a new combined frame. This is done in FIG. 4, process block 414, where the process selects a first subset of the image sensor data from the first frame and a second subset of the image sensor data from the second frame. The subsets are selected as shown at block 416 with the second subset including a different frame portion than the first subset, the first and second subsets including data resulting from the simultaneous exposure of the first and second frames. An example of this is shown in FIG. 3, where the first subset of data out of frame F0 is shown labeled as A1, including data from the second half of the array in this version. The second subset A2 is shown selected out of the second frame F1, where the second subset of data is from the first half of the array.

Preferably, the image sensor is set to the maximum exposure of one frame minus the gap where it cannot be exposed. As the CCU has control over the light source, light pulses are prohibited outside the time window of A1 and A2, as can be seen in FIG. 3 where the pulses p0 and p4 are omitted (as shown by the X over the depicted pulse) from the regular sequence of pulses for the depicted two frames. The gap of time in which the lines are not exposed leads to non equal exposure of lines among the frame. For example, the timing of P2 is such that the scan of line 5 (f0, l5 and f1, l5) is not exposed by pulse p2, and therefore the process includes applying a gain adjustment to the data of line 5. Similarly pulse P3 may fall in the gap for line 8, and adjustment may be applied. In order to accomplish such adjustment, the CCU keeps track of when the frame line is not exposed, e.g., during the gap, and the LED creates a light pulse for a certain period of time for each frame line. When the two frames are combined at block 418, the CCU preferably compensates for this loss of exposure by adding a specific digital gain to each frame line, i.e. a line gain $C_{LINE}$. If this is not done, a pattern would be seen of less and more exposed lines among the frame.

As can be seen on the diagrams of FIG. 2 and FIG. 3, a rolling shutter type array has the disadvantage that a single strobe in each frame does not provide sufficient exposure for all lines to be exposed and read for a single frame. In the depicted process, in order to have an exposure that is longer than only one frame minus the exposure gap, subsets from two frames are added together. This provides a virtual longer exposure and new virtual frame rate of half of the real frame rate coming out of the image sensor. Referring again to FIG. 4, at block 418 the process combines the image sensor data from the first and second subsets A1 and A2 to create a combined frame based on the first and second frames. The CCU feeds the combined frame to the display as part of a video feed and may also record the video feed to non-transitory memory.

Then the process returns to block 406 where it continuously updates the base frequency employed in determining the strobe rate and continues to process the next frame of images for a video stream. As can be seen in FIG. 3, the first and second subsets of image data A1 and A2 can be selected out of a continuous series of frames one after the other. In a preferred version, the two adjacent frames f0 and f1 as shown are exposed with the depicted pulses, with the subsets of data extracted and combined to form a single frame, and the remaining data (in this version, the depicted data not inside the shaded areas of A1 and A2) is discarded. This produces one display frame for every two scanned frames from the image sensor, effectively halving the frame rate from the sensor. For example, a 60 fps sensor would produce a 30 fps video stream with such a method. Typically, the CCU would still drive the display with the refresh rate of the display, which might be higher than half the frame rate of the image sensor. The next frame in the series of FIG. 3 would be a combination based on f2 and f3, not f1 and f2, because the frame rate would have to align evenly to build again a full frame out of two half frames, without influencing or exposing the previous sequence of frame f0 and f1. It is noted that the process only adjusts the base frequency after processing two frames for combination, such that the combined frames are illuminated strobed at the same frequency.

As can be understood, for subsequent frames the process includes creating subsequent two or more light emitter pulses for subsequent image frames spaced in time from the pulses of the first and second image frames according to integer multiples of a time period that is the inverse of the base frequency of the vocalization. The process may further include adjusting a digital gain applied to the image data based on how many pulses of light are employed in exposing each particular line of the rolling shutter readout in the subsequent frames, given that the relative location of the pulses within the subsequent frames will change over time. If the base frequency of the vocalization changes over time, the time period is adjusted to the inverse of the new frequency, but only applied to the consecutive pair of two frames.

As can be seen in the example version of FIG. 3, the first subset A1 includes only data scanned in a second-half period of reading the first frame, and the second subset A2 includes only data scanned in a first-half period of reading the second frame. It is understood that the halves may share a bordering image sensor array line such as the depicted line L5 from which is read data for both subsets, in different frames.

Between a pair of two consecutive combined frames, a slight offset or phase delay to the time interval of the pulses may be made to allow the vocal cord position to be slightly offset between a pair of frames, causing the sequence of frames to appear as slow-motion movement typical of laryngeal stroboscopy.

As can be understood, the process described allows a stroboscopic analysis of vocal cords synchronized in frequency to be performed with a rolling shutter type image array, instead of being limited to a global exposure type shutter arrangement. It is assumed that the camera head or videoendoscope is not moved during this stroboscopy mode, because this would lead to smearing of the image.

Because digital cameras and stroboscopic devices and related circuitry for signal capture and processing are well-known, the present description will be directed in particular to elements forming part of, or cooperating more directly with, a method and apparatus in accordance with the invention. Elements not specifically shown or described herein are selected from those known in the art. Certain aspects of the embodiments to be described are provided in software. Given the system as shown and described according to the invention in the following materials, software not specifically shown, described or suggested herein that is useful for implementation of the invention is conventional and within the ordinary skill in such arts.

Figure 5:
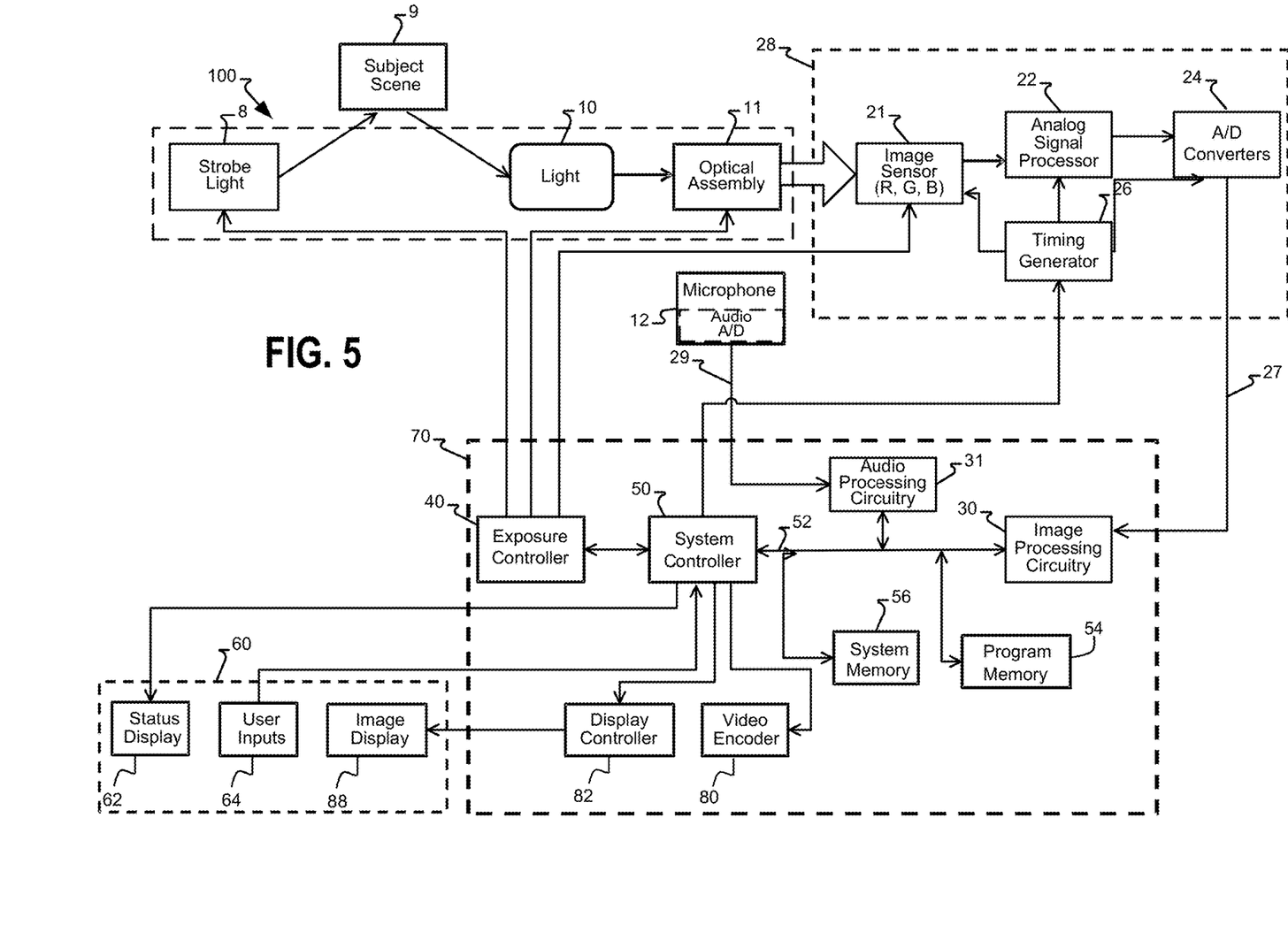
FIG. 5 is a hardware block diagram of an example system including a medical scope, a camera control module, and an electronic display.

Referring to FIG. 5, shown is a system hardware block diagram of an example system including a medical scope 100, a camera control module 70, and a user interface 60 including one or more displays, the system being one example hardware design on which the laryngeal stroboscopy techniques described herein may be implemented. The medical scope 100 in this system is a dual mode stroboscopic laryngoscope with a continuous light mode and a strobing light mode; however, this is not limiting, and the features and techniques herein may be employed with other stroboscopic endoscopes. Of the depicted blocks, scope 100 includes the optical assembly 11 and the camera head and handle 28 ("camera head", "handle") which may be detachable from the scope shaft or may be integrated with the shaft as in the scope of FIG. 1. In other examples, the scope 100 may include a video endoscope having an imager at the distal end of the shaft rather than in a camera head or handle. The scope may also include the light source 8, preferably an LED light source positioned at the tip of the scope shaft such that it illuminates the vocal cords when in inserted in a position like that of FIG. 1.

The light source 8, typically an LED emitter, illuminates subject scene 9. Light source 8 may include a single or multiple light emitting elements configured to provide light throughout the desired spectrum. Further, light source 8 may include fiber optics passing through the body of the scope, or other light emitting arrangements such as LEDs or laser diodes positioned at or near the front of the scope. The light source may also be an external light source or part of the CCU 70, which provides the light for rigid endoscopes. As shown in the drawing, light 10 reflected from the subject scene is passed to an optical assembly 11, where the light is focused toward an image sensor assembly to form an image at a solid-state image sensor(s) 21. Optical assembly 11 includes at least one lens, which may be a wide-angle lens element such that optical assembly 11 focuses light which represents a wide field of view. Portions of the optical assembly may be embodied in a camera head 28, while other portions are in an endoscope shaft. In some embodiments of the invention, the scope handle 28 contains control electronics but the image sensor(s) is located in the scope shaft itself, often toward the distal end of the shaft. The optical assembly 11 may be contained in a single imaging device with the image sensor assembly. Image sensor 21 (converts the incident light to an electrical signal by integrating charge for each picture element (pixel). The image sensor 21 may be a complementary metal oxide semiconductor active pixel sensor (CMOS APS) or a charge-coupled device (CCD), or another suitable image sensor.

Timing generator 26 produces various clocking signals to select rows and pixels and synchronizes the operation of image sensor 21, analog signal processor 22, and A/D converter 24 according to the timing described above with regard to FIGS. 2-4. The image sensor assembly typically includes the image sensor 21, the analog signal processor 22, the A/D converter 24, and the timing generator 26. The functional elements of the image sensor assembly can be fabricated as a single integrated circuit as is commonly done with CMOS image sensors or they can be separately fabricated integrated circuits.

The total amount of light 10 reaching the image sensor 21 is regulated by the light source 8 intensity, an aperture of the optical assembly 11, the time for which the image sensor 21 integrates charge, and the number of strobe pulses dependent on the vocal cord base frequency in stroboscopy mode. An exposure controller 40 responds to the amount of light available in the scene given the intensity and spatial distribution of digitized signals corresponding to the intensity and spatial distribution of the light focused on image sensor 21.

Analog signals from the image sensor 21 are processed by analog signal processor 22 and applied to analog-to-digital (A/D) converter 24 for digitizing the analog sensor signals. The digitized signals each representing streams of images or image representations based on the data, are fed to image processor 30 as image signal 27.

Figure 4:
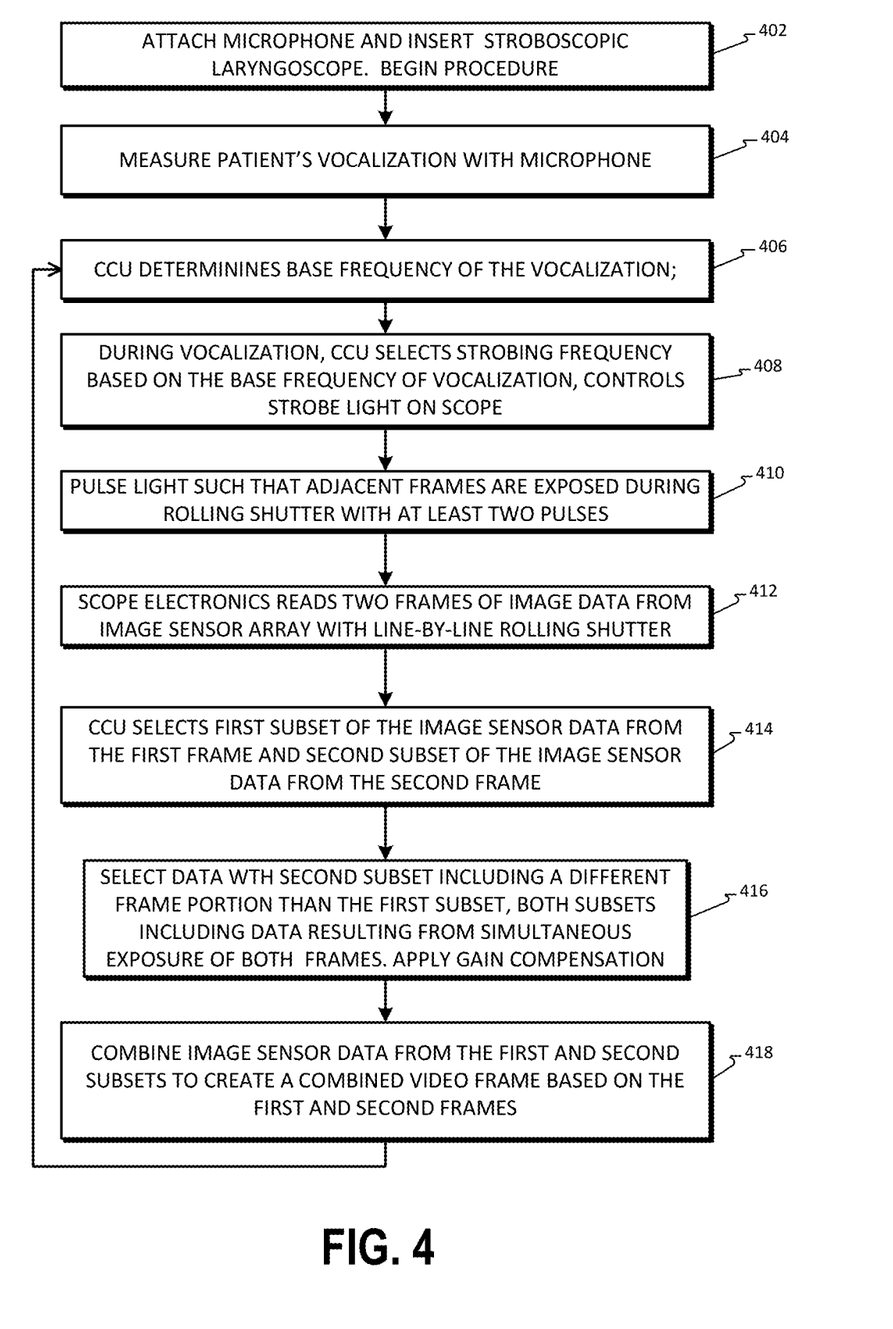
FIG. 4 shows a flowchart of a process for controlling a stroboscopy system and processing data therefrom.

Image processing circuitry 30 includes circuitry for extracting the subsets of image data as described according to the process of FIG. 4 and combining the image data subsets to create combined image frames. This may be done in programmable hardware or in one or more digital signal processing cores programmed with suitable firmware (modules). Image processing circuitry 30 preferably includes a gain processing module that applies a digital line gain to values on one or more lines in the first and second subsets to compensate for a loss of exposure due to a time gap between the first and second adjacent frames according to the processes described herein. Image processing circuitry 30 also includes circuitry performing digital image processing functions to process and filter the received images as is known in the art.

Audio processing circuitry 31 receives the audio signal from microphone 12, which in use is positioned on or near the patient. The microphone may include an A/D converter to digitize the audio signal or such conversion may be made by the CCU audio processing circuitry 31. Typically the audio processing circuitry is implemented in either a DSP or FPGA/coprocessor arrangement, and performs digital fast Fourier transforms (FFT) and frequency domain analysis in order to measure the audio power levels at each frequency in the audio signal and determine the base frequency of the patient vocalization. Such circuitry is known in the art of stroboscopic laryngoscopes and will not be further described. Typically, audio processing circuitry 31 is implemented on the same device as image processing circuitry 30.

The system controller 50 controls the overall operation of the image capture device based on a software program stored in program memory 54. This memory can also be used to store user setting selections and other data to be preserved when the camera is turned off. System controller 50 controls the sequence of data capture by directing exposure controller 40 to set the light source 8 intensity, controls the pulsing of light source 8 when in strobing mode, controls the optical assembly 11 aperture, and controls various filters in optical assembly 11 and timing that may be necessary to obtain the image stream. A data bus 52 includes a pathway for address, data, and control signals.

Processed image data are continuously sent to video encoder 80 to store data for later review of the procedure by the user. The processed image data is also formatted by display controller 82 and presented on image display 88. This display is typically a liquid crystal display backlight with light-emitting diodes (LED LCD), although other types of displays are used as well. The processed image data can also be stored in system memory 56 or other internal or external memory device.

The user interface 60, including all or any combination of image display 88, user inputs 64, and status display 62, is controlled by a combination of software programs executed on system controller 50, receiving input from user inputs 64 and from buttons positioned on the scope handle 28. User inputs 64 typically include some combination of typing keyboards, computer pointing devices, buttons, rocker switches, joysticks, rotary dials, or touch screens. The system controller 50 manages the graphical user interface (GUI) presented on one or more of the displays (e.g. on image display 88). In particular, the system controller 50 will typically have a mode toggle user input (typically through a configurable button on the endoscope or camera head itself, but possibly through a GUI interface), and in response transmit commands to adjust image processing circuitry 30 based on predetermined setting stored in system memory. Preferably a system employed with any of the device designs herein provides ability to toggle between at least two modes, continuous light mode and strobing mode.

Image processing circuitry 30 is one of three programmable logic devices, processors, or controllers in this embodiment, in addition to a system controller 50 and the exposure controller 40. Image processing circuitry 30, controller 50, exposure controller 40, system and program memories 56 and 54, video encoder 80 and display controller 82 may be housed within camera control unit (CCU) 70.

CCU 70 may be responsible for powering and controlling light source 8, the image sensor assembly, and/or optical assembly 11, and may power and receive signals directly from the buttons on the scope 100, or indirectly if the buttons pass their signals through a controller in the camera head such as the analog signal processor. Such power and control connections are not depicted separately but will typically be contained in a single flexible cable with data connection 27.

Figure 6:
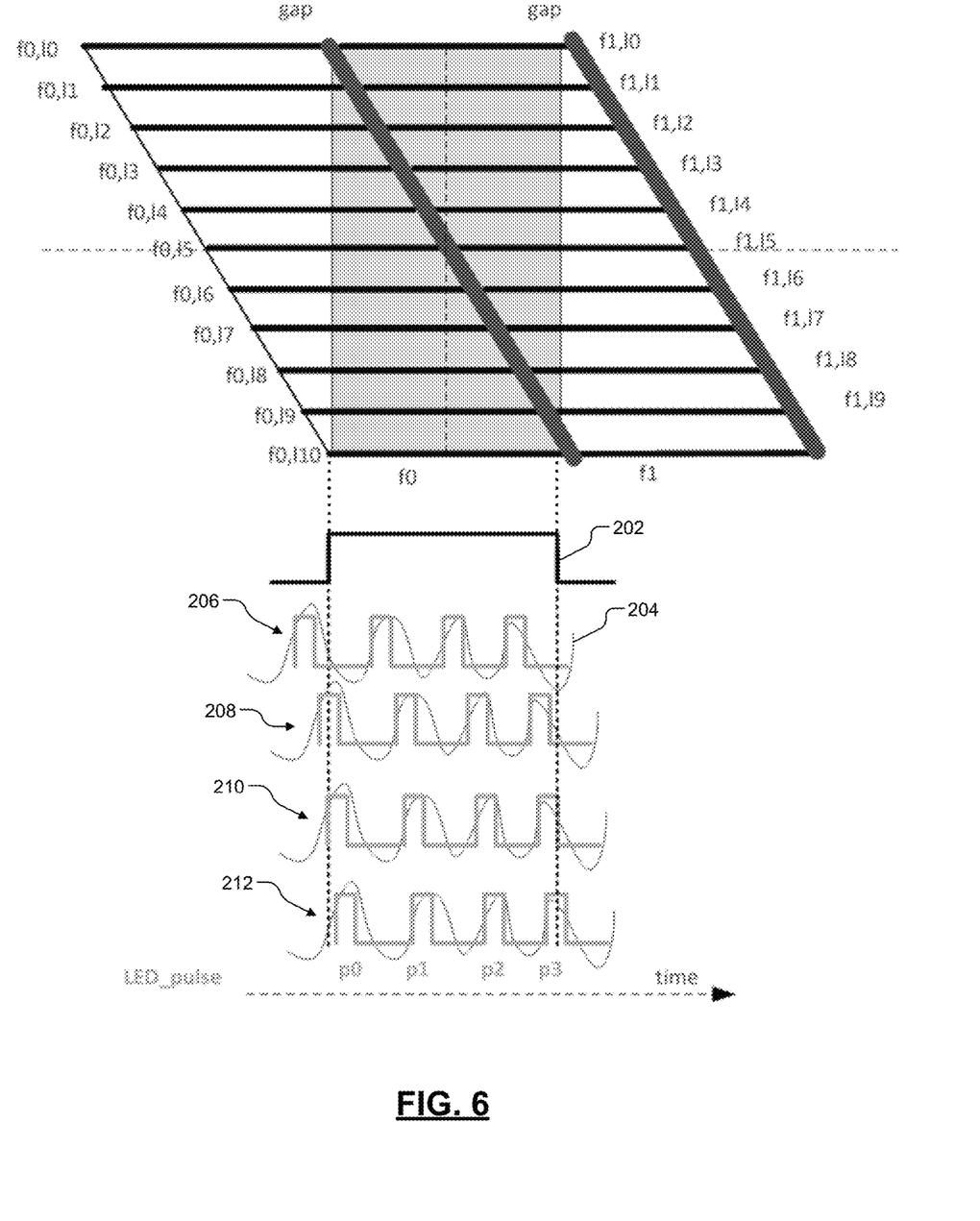
FIG. 6 shows timing diagrams for a process of strobing the light source during a gate time with various examples of light pulse sets.

Referring back to FIGS. 2 and 3, and now also to FIG. 6, the total amount of light emitted from LED pulses (p0-p3) during the time window encompassing portions A1 and A2 may vary depending on the phase. As shown in FIG. 6, this time window forms a gate time 202. Ideally, complete pulses would fall within this gate time 202. However, in some situations, partial pulses are possible which could lead to whole combined frames being under or over exposed compared with prior or later frames. Examples of light pulse sequences with partial pulses are described below.

Four different sets of LED pulses as indicated by arrowed pointers 206-212 are shown for illustration purposes only. Each set of LED pulses also includes three to four pulses for illustration purposes only. Each set represents a possible LED pulse sequence which may occur during any one particular gate 202 in a sequence of frames. The LED pulses are shown as square-edge traces representing near instantaneous "on" and "off" cycling common to LED light sources during a stroboscopy procedure. A first pulse set 206 may include three full pulses of the same duration that occur within the gate time 202 and a leading pulse not occurring within the gate time 202. A second pulse set 208 may include one partial pulse followed by three full pulses of the same duration occurring within the gate time 202. A third pulse set 210 may include four full pulses all occurring within the gate time 202. A fourth pulse set 212 may include three full pulses followed by a final partial pulse occurring within the gate time 202.

The total duration of time during which light is projected from the LED light source will vary for each of the four different sets of LED pulses. For example, frame f0 and frame f1 may include the first pulse set 204 while subsequent frames f2 and f3 (not shown) may include the second pulse set 206. Alternately, any of the LED pulse sets 204-210 or others not shown (with fewer or more pulses) may occur during any of the frames f0 through f3 or any additional frames f(n) thereafter. This may lead to unwanted "flicker" in the image stream when viewed as a video output. For example, the third pulse set 210 may produce the "brightest" combined frame while the first pulse set 206 may produce the "darkest" combined frame.

One solution to this problem includes applying an overall gain to the output frame based on the actual amount of light captured by the imager from the pulses during the gate time 202 and a desired amount of light. For example, the duration of a light pulse $T_{LED}$ may be set as a fraction F of the period of the audio signal from the vocalization. In one application, the fraction F could be set to 0.07 which would mean the LED is "on" for 7% of the audio signal period. Because of the phasing of the audio signal, the total amount of light from the LED pulses being "on" during the time window or gate time $T_{GATE}$ can vary over time. Notably, this may occur when a vocalization changes frequency based on the physician's instructions to the patient. The varying amount of light from frame to frame may appear as flicker in the intensity or brightness of the final video output to the display 88.

The maximum amount of LED "on" time that can fall within the gate time $T_{GATE}$ may be fixed as $T_{GATE}*F$ for any given desired audio frequency of the vocalization during the gate time. This may be a user preset for example. The intensity of the video can then be compensated by applying an overall frame gain to output frames. The frame gain would be a multiplier to adjust brightness of every pixel in a given output frame. For example, the frame gain may include a gain compensation factor $C_{FRAME}$ calculated by dividing $T_{GATE}*F$ by the actual amount of time the LED pulses were "on," $T_{PULSE}$, during the gate time $T_{GATE}$. That is $C_{FRAME}=T_{GATE}*F/T_{PULSE}$.

In some examples, $T_{PULSE}$ might exceed $T_{GATE}*F$. In such situations, the gate time $T_{GATE}$ may be closed early when $T_{PULSE}$ approaches or equals $T_{GATE}*F$. This will ensure that the gain compensation factor $C_{FRAME}$ is always greater than or equal to 1.0. Gains less than 1.0 may cause interscene clipping artifacts.

Figure 7:
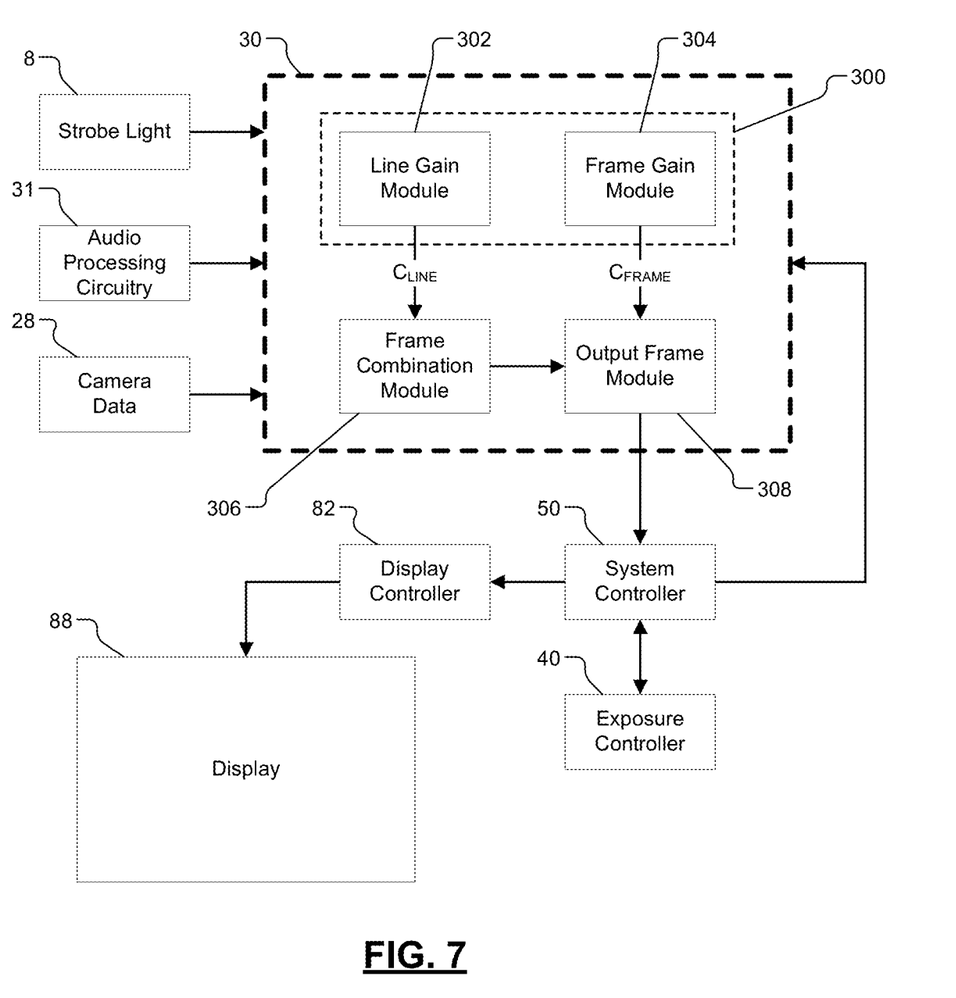
FIG. 7 is a hardware block diagram of an example subsystem of the medical scope, camera control module, and the electronic display of FIG. 5.

Referring now to FIG. 7, the exemplary image processing circuitry 30 may determine the appropriate gains for both the line gain $C_{LINE}$ and the frame gain $C_{FRAME}$. For example, the gain processing module 300 may include a line gain module 302 and a frame gain module 304. The line gain module 302 may determine a line gain to be applied to each line L0-L10 due to the gap between the combined portions A1 and A2 of frames f0 and f1. For example, the line gain module 302 may determine the line gain value based on the gap time and pulse position in time. The frame gain module 304 may determine an overall frame gain to be applied to each combined frame made up of portions A1 and A2 due to the amount of each LED pulse that appears during the gate 202 of the combined frame. For example, the frame gain module 304 may determine the combined frame gain value based on the gain compensation factor $C_{FRAME}$. The line gain module 302 may output the line corrected portions A1 and A2 to a frame combination module 306 which combines the portions A2 and A2 into a combined frame. The combined frame may be output to an output frame module 308 which subsequently applies the overall frame gain to the combined frame to reduce flicker and produce a final processed frame. The final process frame may then appear without flicker.

Figure 8:
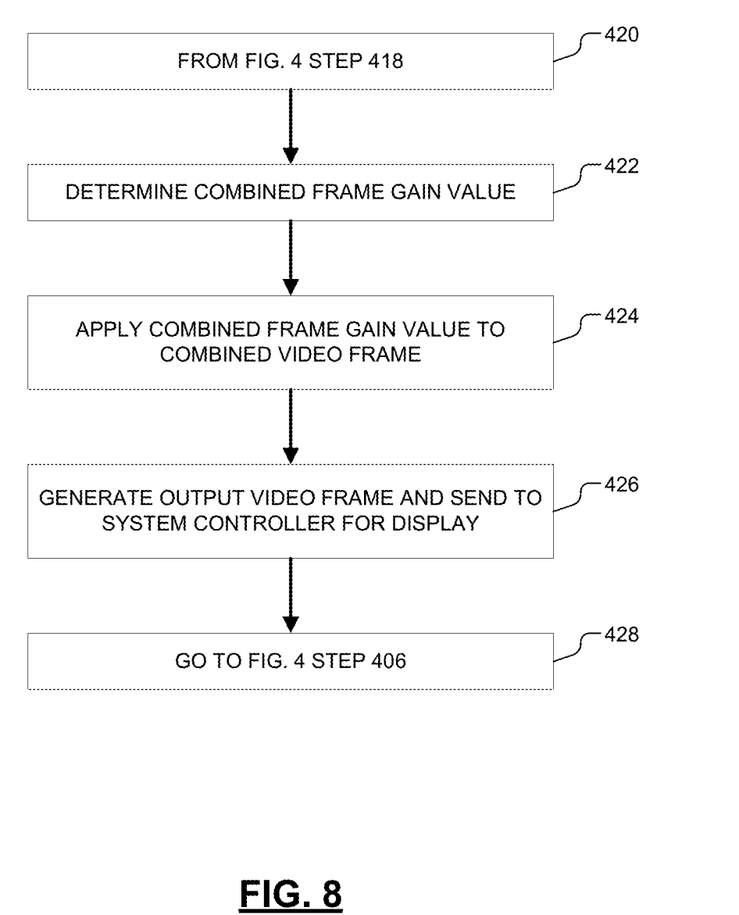
FIG. 8 shows a flowchart of another process for controlling the stroboscopy system and processing data therefrom.

In FIG. 8, additional steps of the exemplary method of FIG. 4 may proceed from step 418 at step 420. In step 422, the gain processing module 300 may determine a combined frame gain value to be applied to the combined frame to compensate for variations in the amount of LED pulse light generated during the gate. For example, as mentioned previously, the frame gain module 304 may determine the frame gain compensation factor $C_{FRAME}$ based on the gate time $T_{GATE}$, the desired amount of light or fraction F of the gate time $T_{GATE}$, and the actual amount of time light was captured, $T_{PULSE}$.

In step 424, the output frame module 308 may apply the combined frame gain value to the combined video frame. For example, each pixel of the combined video frame with portions from A1 and A2 may be increased in brightness, decreased in brightness, or kept substantially the same. In step 426, the output frame module 308 may generate an output video frame based on the combined frame gain value and the combined video frame and send the output video frame to the system controller 50 for eventual display by the display controller 82 on the display 88. The method continues with step 406 to complete the loop and determine again the base frequency of the vocalization.

Although this distribution of imaging device functional control among multiple programmable logic devices, processors, and controllers is typical, these programmable logic devices, processors, or controllers can be combinable in various ways without affecting the functional operation of the imaging device and the application of the invention. These programmable logic devices, processors, or controllers can comprise one or more programmable logic devices, digital signal processor devices, microcontrollers, or other digital logic circuits. Although a combination of such programmable logic devices, processors, or controllers has been described, it should be apparent that one programmable logic device, digital signal processor, microcontroller, microprocessors or other digital logic circuit can be designated to perform all of the needed functions. All of these variations can perform the same function and fall within the scope of this invention.

As used herein the terms "comprising," "including," "carrying," "having" "containing," "involving," and the like are to be understood to be open-ended, that is, to mean including but not limited to. Any use of ordinal terms such as "first," "second," "third," etc., in the claims to modify a claim element does not by itself connote any priority, precedence, or order of one claim element over another, or the temporal order in which acts of a method are performed. Rather, unless specifically stated otherwise, such ordinal terms are used merely as labels to distinguish one claim element having a certain name from another element having a same name (but for use of the ordinal term).

The foregoing has outlined rather broadly the features and technical advantages of the invention in order that the detailed description of the invention that follows may be better understood. It should be appreciated by those skilled in the art that the conception and specific embodiments disclosed may be readily utilized as a basis for modifying or designing other structures for carrying out the same purposes of the invention. It should also be realized by those skilled in the art that such equivalent constructions do not depart from the scope of the invention as set forth in the appended claims.

Although the invention and its advantages have been described in detail, it should be understood that various changes, substitutions and alterations can be made herein without departing from the scope of the invention as defined by the appended claims. The combinations of features described herein should not be interpreted to be limiting, and the features herein may be used in any working combination or sub-combination according to the invention. This description should therefore be interpreted as providing written support, under U.S. patent law and any relevant foreign patent laws, for any working combination or some sub-combination of the features herein.

Moreover, the scope of the present application is not intended to be limited to the particular embodiments of the process, machine, manufacture, composition of matter, means, methods and steps described in the specification. As one of ordinary skill in the art will readily appreciate from the disclosure of the invention, processes, machines, manufacture, compositions of matter, means, methods, or steps, presently existing or later to be developed that perform substantially the same function or achieve substantially the same result as the corresponding embodiments described herein may be utilized according to the invention. Accordingly, the appended claims are intended to include within their scope such processes, machines, manufacture, compositions of matter, means, methods, or steps.

The invention claimed is:

1. A video endoscopy system comprising:
an imager that generates a first frame and a second frame of a plurality of video frames using a rolling shutter;
a light source that generates pulses of light based on a desired frequency;
an exposure controller that adjusts a duration and position in time of the pulses based on the desired frequency during the first and second frames; and
a digital line gain module that selectively applies a digital line gain to at least a portion of the first frame and a portion of the second frame, the digital line gain applied to pixels on one or more lines of the portions of the first and second frames, based on a gap time between the first frame and the second frame and the duration and position in time of the pulses.

2. The video endoscopy system of claim 1, further comprising a frame gain module that selectively applies a digital frame gain to a combined frame generated from the portions of the first and second frames, the digital frame gain applied to pixel values of the combined frames, based on the duration of the pulses and a desired duration of the pulses.

3. The video endoscopy system of claim 1, wherein the light source generates two or more light pulses during the first and second frames.

4. The video endoscopy system of claim 1, wherein the first and second frames are adjacent frames.

5. The video endoscopy system of claim 2, further comprising a frame combination module that combines portions of the first and second frames to form the combined frame after application of the digital line gain.

6. The video endoscopy system of claim 5, further comprising an output frame module that generates an output frame based on the digital frame gain and the combined frame.

7. The video endoscopy system of claim 1, further comprising audio processing circuitry that determines the desired frequency using a vocalization based on an audio signal.

8. A method of operating a video endoscopy system comprising:
  generating a first frame and a second frame of a plurality of video frames using a rolling shutter;
  generating pulses of light at a desired frequency;
  adjusting a duration and position in time of the pulses based on the desired frequency during the first and second frames; and
  selectively applying a digital line gain to at least a portion of the first frame and a portion of the second frame, the digital line gain applied to pixel values on one or more lines of the portions of the first and second frames, based on a gap time between the first frame and the second frame and the duration and position in time of the pulses.

9. The method of operating a video endoscopy system of claim 8, further comprising selectively applying a digital frame gain to a combined frame generated from the portions of the first and second frames, the digital frame gain applied to pixel values of the combined frame, based on the duration of the pulses and a desired duration of the pulses.

10. The method of operating a video endoscopy system of claim 8, further comprising generating two or more light pulses during the first and second frames.

11. The method of operating a video endoscopy system of claim 8, wherein the first and second frames are adjacent frames.

12. The method of operating a video endoscopy system of claim 9, further comprising combining portions of the first and second frames to form the combined frame after application of the digital line gain.

13. The method of operating a video endoscopy system of claim 12, further comprising generating an output frame based on the digital frame gain and the combined frame.

14. The method of operating a video endoscopy system of claim 8, further comprising determining the desired frequency using a vocalization based on an audio signal.

* * * * *